United States Patent
Bernaz

[11] Patent Number: 5,849,009
[45] Date of Patent: Dec. 15, 1998

[54] FLEXIBLE PROBE FOR HIGH FREQUENCY SKIN TREATMENT

[76] Inventor: Gabriel Bernaz, 35, rue Marziano, 1227 Carouge, Switzerland

[21] Appl. No.: 776,666

[22] PCT Filed: Jul. 24, 1995

[86] PCT No.: PCT/EP95/02930

§ 371 Date: Jan. 31, 1997

§ 102(e) Date: Jan. 31, 1997

[87] PCT Pub. No.: WO96/03928

PCT Pub. Date: Feb. 15, 1996

[30] Foreign Application Priority Data

Aug. 2, 1994 [EP] European Pat. Off. .............. 94810452

[51] Int. Cl.$^6$ .................................................. A61B 17/41
[52] U.S. Cl. ............................................... 606/36; 606/41
[58] Field of Search .................................. 606/9, 10, 13, 606/27, 28, 32, 41, 43, 36; 607/96, 98, 99, 97

[56] References Cited

U.S. PATENT DOCUMENTS

| | | | |
|---|---|---|---|
| 3,202,801 | 8/1965 | Saluri ......................................... | 607/96 |
| 3,889,101 | 6/1975 | Woods ...................................... | 607/96 |
| 3,994,300 | 11/1976 | Siddons .................................... | 606/36 |
| 4,028,518 | 6/1977 | Boudouris et al. ....................... | 607/98 |
| 4,167,187 | 9/1979 | Biagi ........................................ | 606/36 |
| 4,498,474 | 2/1985 | Chalmers et al. ........................ | 606/36 |
| 4,784,136 | 11/1988 | Klein ......................................... | 606/36 |
| 5,182,857 | 2/1993 | Simon ........................................ | 606/9 |
| 5,364,394 | 11/1994 | Mehl ......................................... | 606/36 |
| 5,425,728 | 6/1995 | Tankovich .................................. | 606/9 |
| 5,669,916 | 9/1997 | Anderson ................................... | 606/36 |

FOREIGN PATENT DOCUMENTS

| | | |
|---|---|---|
| 2114947 | 3/1993 | Canada . |
| 2132892 | 7/1984 | United Kingdom . |

*Primary Examiner*—Jennifer Bahr
*Assistant Examiner*—Sonya Harris-Ogugua
*Attorney, Agent, or Firm*—Thomas J. Engellenner; Faustino A. Lichauco; Lahive & Cockfield, LLP

[57] ABSTRACT

An applicator probe (10) for applying a high-frequency electromagnetic energy flux to the skin through a conducting gel, the applicator probe having a non-conducting contact surface (14) which is applied to the skin. This surface includes a plurality of discrete electromagnetic emission points or areas (16) defined by parts of the turns of a coil (12) which is set back from the surface when the applicator probe is in use. The applicator probe according to the invention consists of a flexible sheet which is able to conform to the part of the body onto which it is applied. The flexible sheet includes a non-conductive lower internal portion (or "sole") and a non-conductive upper/external portion (or "back"). At least the lower portion is a sole (14) provided with a row of cavities and which forms the contact surface. The cavities contain the conducting gel which is applied to the skin. The generally flat turns of the coil are arranged in a sandwich configuration between the openwork sole (14) and the back.

16 Claims, 4 Drawing Sheets

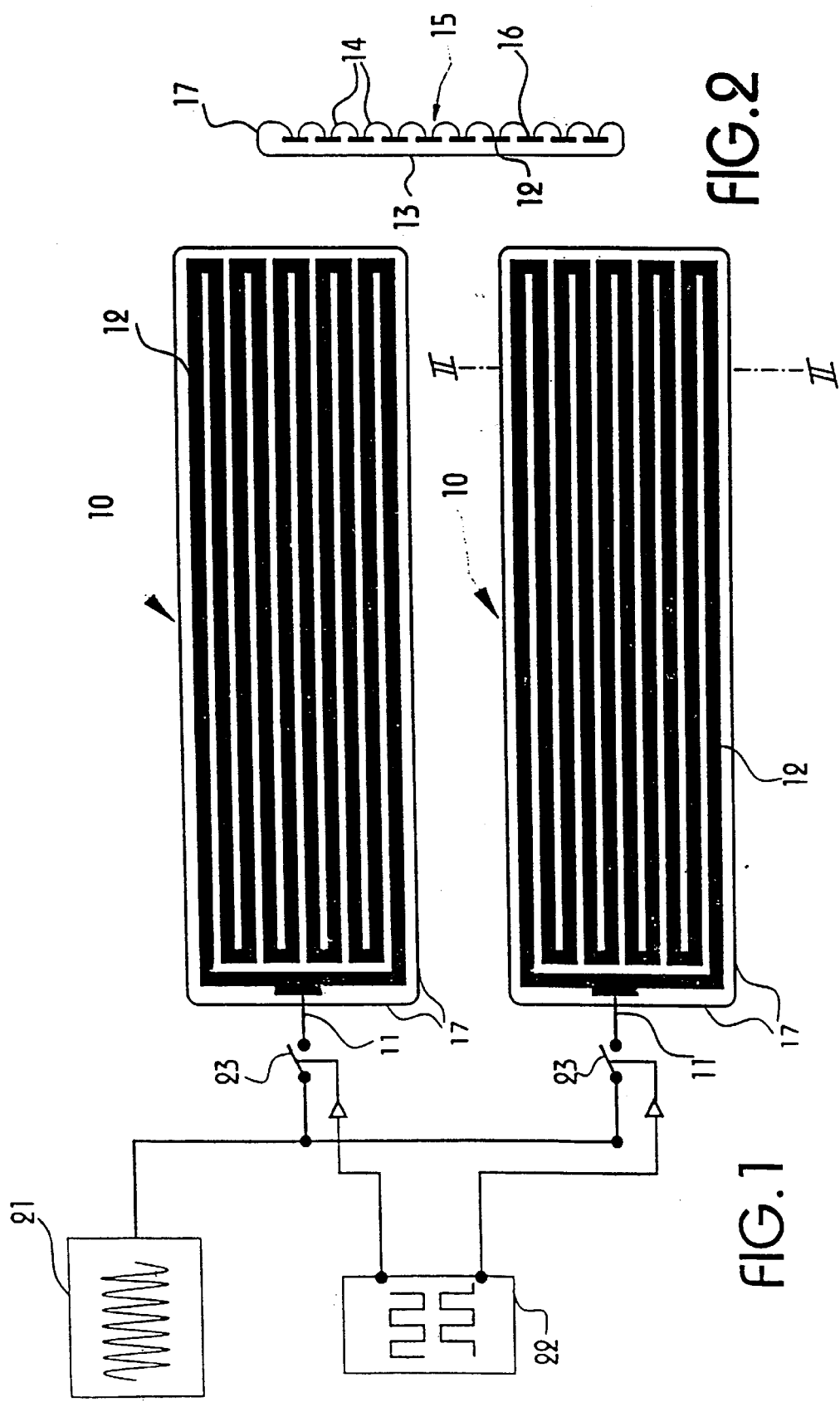

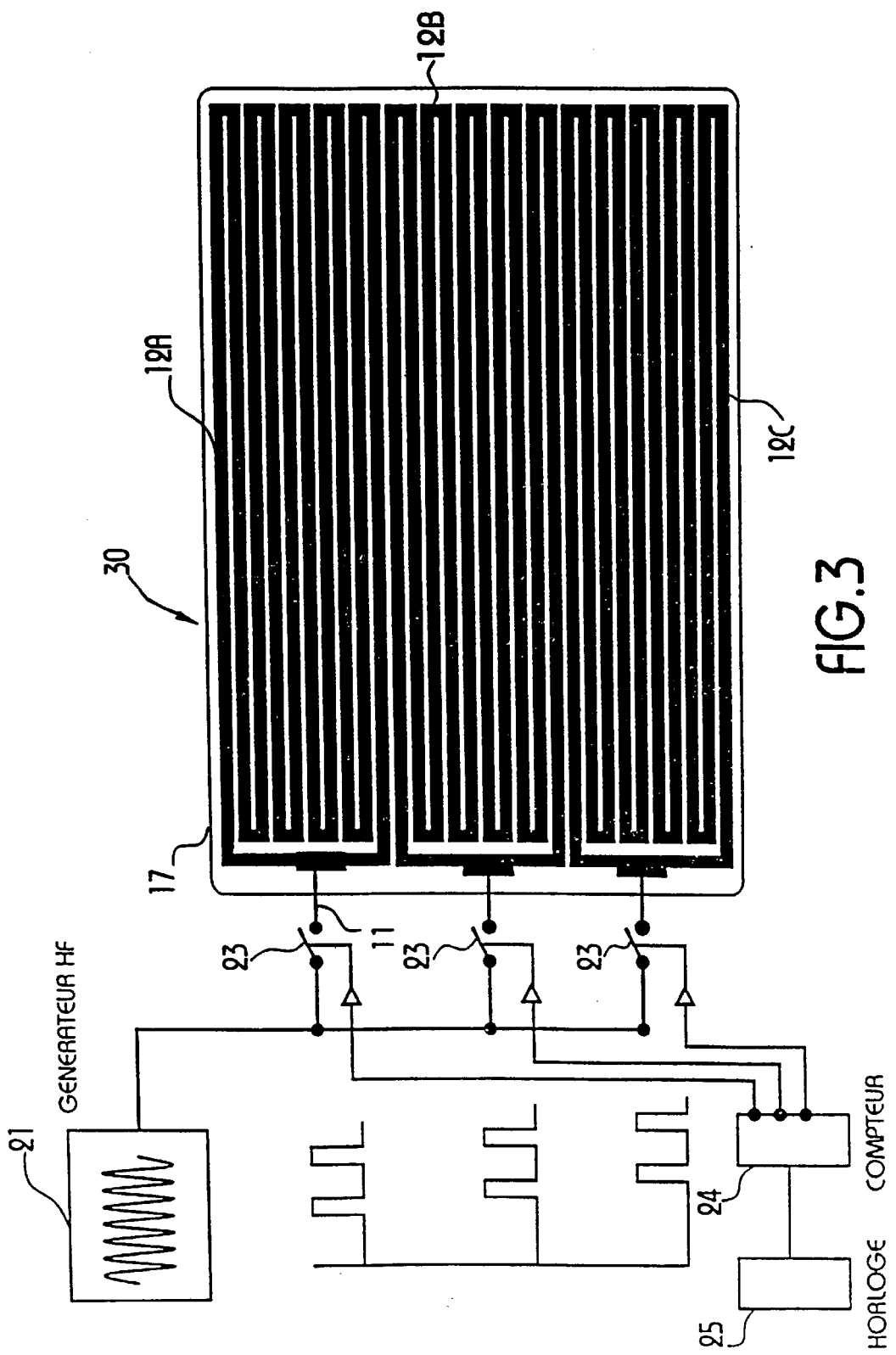

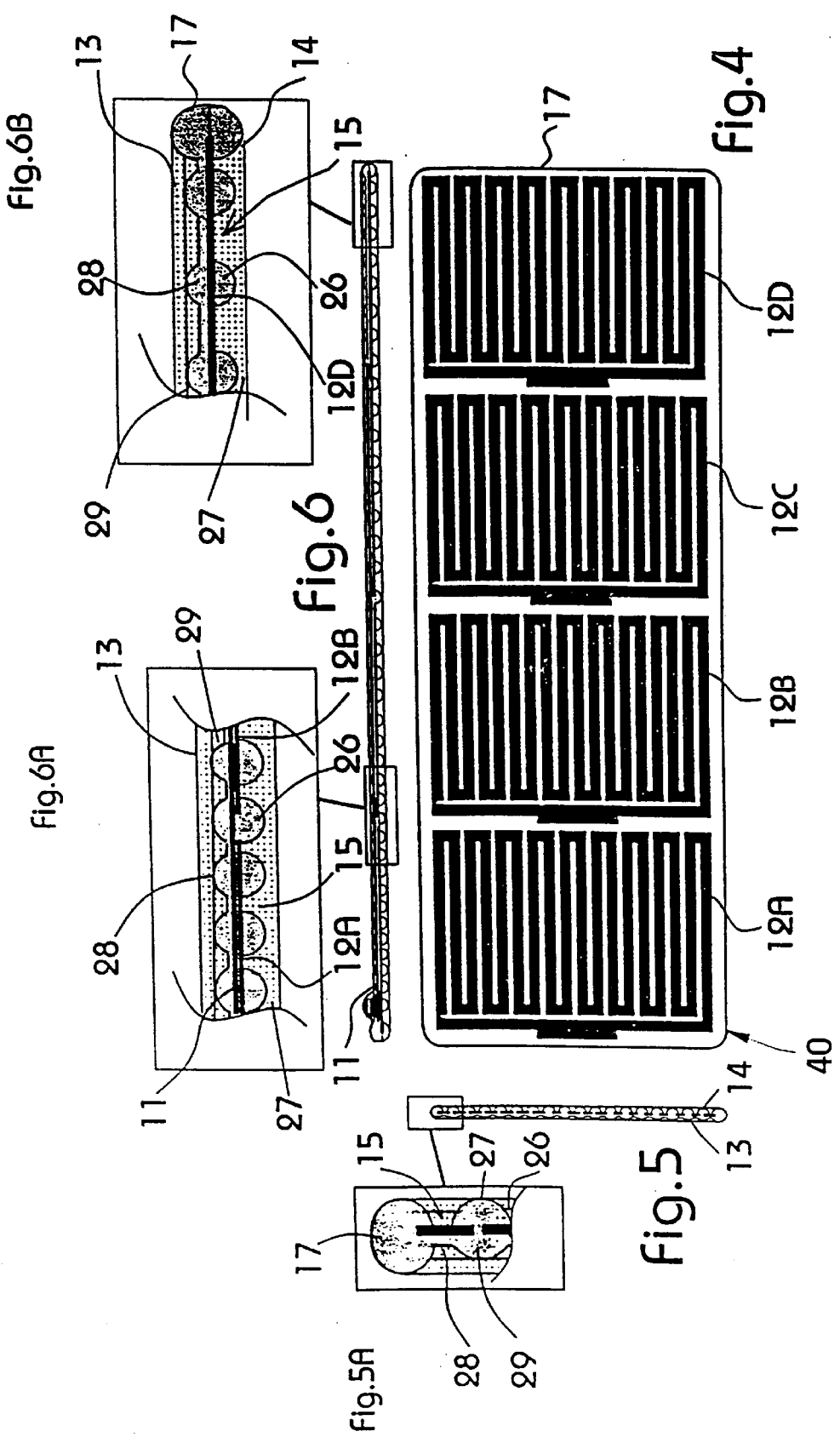

FLEXIBLE PROBE FOR HIGH FREQUENCY SKIN TREATMENT

The invention relates to treatment of the skin by high-frequency electric means, particularly for so-called "permanent" or "long lasting" depilation, as well as for regrowth of hair.

STATE OF THE ART

WO 93/0463 describes a method based on the observation that by mixing a conductive gel of a usual type suitable for coupling ultrasound probes with the skin with a treating product, for example a lotion for producing atrophy of the hair roots, it was possible by high-frequency transcutaneous induction to cause the treating product to penetrate into the hair follicles (pores) and hence carry out a treatment.

This method hence enables a treatment of the skin to be carried out, notably a cosmetic treatment, for example to achieve long lasting depilation, and which moreover allows a punctual and effective application down to the follicles without a delicate manual intervention. The same technique is also suitable for introducing other cosmetic products into the skin, for example for hair regrowth, or against wrinkles, as well as pharmaceutical products, for example for treating achne, seborrhea, wounds, or pains.

To carry out the method, WO 93/04636 also describes an apparatus comprising a handleable member, for contacting the skin, having a non-conductive body provided with a contact surface adapted to be applied to the skin. This surface comprises a plurality of discrete conductive electromagnetic emission points, for example formed by exposed parts of turns of a solenoid embedded in the body of the contact member. These points are accessible through openings in this surface and are preferably set back with respect to the latter, so that during use of the apparatus, these points may contact conductive gel applied to the skin. These discrete emission points emit a high-frequency flux of electromagnetic energy, advantageously a pure emissive current, supplied by a high-frequency oscillatory power circuit.

The handleable member of the above-described apparatus thus forms a focalised probe whose high-frequency energy produces a pointwise action through the loaded gel. By arranging the discrete emission points in a suitable manner on the contact surface, a simultaneous action is obtained on all of the follicles of an area of the skin. For example, the discrete emission points are aligned in one or several rows along an oblong contact surface whose dimensions are adapted to the part of the body to be treated. Preferably, several interchangeable rigid contact members are provided having contact surfaces of different shapes and/or of different sizes, and possibly also an interchangeable needle fitment, thus enabling treatments suitable for all types of pilosity.

The high-frequency electric generator circuit of the apparatus advantageously comprises a high-frequency oscillatory power circuit comprising a transistor connected as a power oscillator in combination with a pair of square-wound self-inductance coils, and an electrode by means of which the impedance of a treated person's body may be added to that of the self-inductance coils to increase the frequency of the emissive current during use.

SUMMARY OF THE INVENTION

The present invention relates to an applicator probe for applying a flux of high-frequency electromagnetic energy to the skin, useful notably in the method described in WO 93/04636 or any other method necessitating application of a conductive gel, this applicator probe being provided with a non-conductive contact surface adapted to be applied to the skin, this surface having a plurality of discrete conductive electromagnetic emissive points or areas formed by parts of turns of a coil which are set back in relation to this surface.

The applicator probe according to the invention is a "morphological" applicator probe, characterized in that it is in the form of a flexible sheet able to conform to the part of the body to which it is applied. This flexible sheet comprises a non-conductive lower/internal part (or "sole") and an upper/external part (or "back"), said contact surface being present at least on said lower part and being provided with cavities. The coil has generally flat turns arranged in sandwich configuration between said lower part (sole) and said upper part (back), with the emissive points or areas arranged at the bottom of the cavities in the contact surface.

When the applicator probe is used, a mixture of gel/active treating product is applied onto the skin to be treated and/or into the cavities of the applicator probe's contact surface so that this mixture acts as conductive interface between the the flexible applicator probe's contact surface and the skin.

The flexible applicator probe according to the invention has numerous advantages. For instance, it can easily be manufactured in all shapes and dimensions suitable for efficient treatment of different parts of the body.

Once the flexible applicator probe has been applied to the body, and after pre-application of the conductive gel onto the applicator probe or the skin, no manual intervention is required during the treatment. It is therefore possible to program the treatment for a predefined duration, which permits optimal penetration of the product, and hence a more efficient treatment. It follows that the flexible applicator probe is suitable not only for the treatment of large surface areas, but also the treatment of small surface areas.

As the applicator probe's flexibility produces good contact even on curved (convex) parts like the arms or legs and on hollowed parts, the applicator probe can be referred to as a morphological applicator probe because it conforms to the morphology of that part of the body under treatment.

By using a sectorial scanning technique, large surface areas can be treated with reduced energy. Moreover, employing two similiar flexible applicator probes each subjected to the sectorial scanning technique enables simultaneous treatment for example of two arms or two legs.

The use of one or several generally flat coils in the (or each) flexible applicator probe enables maximum use to be made of the coil's surface for transmitting the electromagnetic flux, thereby considerably increasing the number of electromagnetic emitting points or areas. With the new flexible applicator probe, it is possible to provide surfaces, for example, with two hundred to two thousand emission points or areas, or even more, whereas with the handleable probe of WO 93/04636, in practice the maximum number of emitting points used is seventy-five, i.e. three rows of twenty-five points.

Advantageously, the applicator probe has a contact surface on its two faces, which increases the flexibility of the applicator probe, hence improving the ease with which it can conform to the parts of the body to which it is applied. Moreover, each of its faces may have cavities whose shapes and/or dimensions and/or distribution are/is different from those on the opposite face.

An alveolar applicator probe provided with cavities of different sizes on its two faces has the advantage of permitting different treatments due to the fact that the skin is exposed to different fluxes of electromagnetic energy depending on the different arrangement of cavities on the two faces, and also permits application of different quantities of the mixture by choice of the face to be used, because of the different sizes of the cavities.

Also, flexible applicator probes according to the invention can be manufactured by a simple molding operation with the generally flat coil(s) arranged in a sandwich configuration between said back and the alveolar or openwork sole, enabling considerable savings relative to the rigid handleable probes used at present.

The turns of the generally flat coil are preferably formed by a conductive sheet of conductive silicone resin, for example containing a silvered sintered glass, or by a conductive sheet of graphite-loaded rubber. It is also possible to use a suitable flexible support printed with metal.

The invention also concerns the use of this flexible applicator probe for long-lasting hair removal and for the treatment of baldness, as well as the use of a gel/conductor mixture as conductive interface between the contact surface of a flexible applicator probe and the skin, and as means for transporting a bioactive product to cause the latter, within a conductive solution derived from the mixture, to penetrate into the follicles in the skin down to the hair roots.

The invention also concerns a cosmetic method of treatment wherein the above-mentioned mixture is applied into cavities in the surface of a flexible applicator probe able to conform to the part of the body to which it is applied, the surface of the flexible applicator probe covered with the mixture is applied onto the skin, and a flux of high-frequency electromagnetic energy is supplied via the cavities of the flexible applicator probe.

According to another inventive aspect relating to a long lasting depilation method, before applying the mixture, the hairs over an area of the skin to be treated are cut, leaving the severed ends of the hairs flush with the surface of the skin. The gel/product mixture is then applied followed by a flux of high-frequency electromagnetic energy to cause the product to penetrate down to the roots of the cut hairs. The treatment is repeated after a rest period, possibly without cutting the hairs again (i.e. cutting the hairs only if desired and/or if necessary) until the hair roots have completely atrophied and the hairs with their roots preferably fall out naturally, for example when being washed.

Further features of the invention and several variations are set out in the dependant claims.

BRIEF DESCRIPTION OF THE DRAWINGS

Further features of the invention will be apparent from the following description, given by way of example, with reference to the drawings in which:

FIG. 1 is a diagram illustrating two flexible applicator probes according to the invention and a control circuit;

FIG. 2 is a cross-section along line II—II of FIG. 1 on an enlarged scale;

FIG. 3 is diagram of an embodiment of the invention comprising three generally flat coils, connected in parallel to a control circuit;

FIG. 4 is a diagram of another embodiment of flexible applicator probe, with two (operative) faces;

FIGS. 5 and 6 are schematic views in transverse cross-section and in longitudinal cross-section of the flexible applicator probe of FIG. 4;

FIGS. 5A, 6A and 6B are enlargements of the framed parts of FIGS. 5 and 6;

PREFERRED EMBODIMENTS

Figure 7:
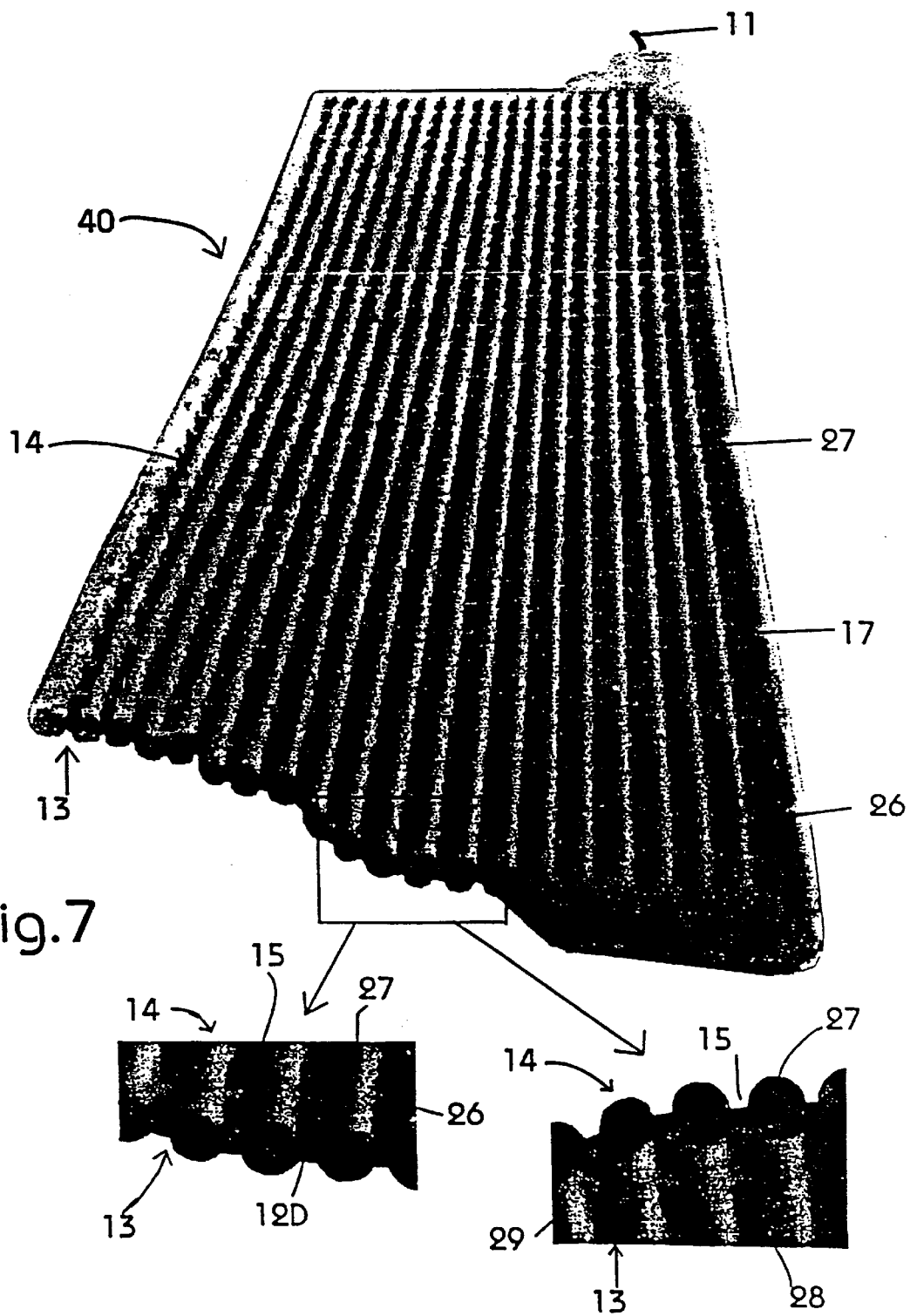
FIG. 7 is a perspective photographic view showing the contact surface of an applicator probe similar to that of FIG. 4, a corner part of the applicator probe having been cut away.

FIG. 1 shows two flexible applicator probes 10 according to the invention, connected in parallel to a control circuit 21. Each flexible applicator probe 10 comprises a current lead-in 11 supplying a generally flat coil 12 formed of generally flat turns, namely five turns in this example. The generally flat coil 12 of rectangualar shape is made in a conductive sheet of silicone resin, for instance containing silvered sintered glass, or in any other electrically conductive flexible sheet.

This generally flat coil 12 is incorporated in a one-piece non-conductive flexible body, for example of rubber, the generally flat turns of the coil 12 being disposed in sandwich configuration between a back or top 13 surface of an imperforate sheet, and an openwork sole or bottom 14, completed by a periphery 17 also of rubber. The openwork sole 14 is made up either of elements extending along the longitudinal parts of the coil 12's turns, or a criss-cross arrangement of elements extending along the longitudinal and transverse parts of the coil 12's turns. For example, for an applicator probe as illustrated whose turns have ten longitudinal parts, from eleven to thirty-one transverse parts can be provided so that there are between one hundred and three hundred orifices 15 through which the exposed parts of the turns are accessible but set back relative to the sole 14's contact surface, forming the emission points or areas 16.

The emission points or areas 16 may for example measure from 0.5 mm to 2 mm across (i.e. the exposed width of the generally flat coil) and from 1 mm to 10 mm long. Usually, the points or areas measure about 1 mm×3 mm, and are arranged in a rectangular rubber part measuring about 4 mm×5 mm.

The applicator probes 10 are thus morphological applicator probes each made up of a flexible rectangular rubber sheet incorporating a generally flat coil 12 whose turns occupy substantially the entire area of the flexible sheet, except its non-conductive periphery 17.

An example of the circuit 21 is described in WO 93/04636 (see FIG. 4). This circuit is housed in a casing and comprises a stabilized double supply followed by an oscillatory circuit delivering at its output a current of low amplitude and very high frequency. Compared to conventional quartz-driven circuits used in this field, and which operate at fixed frequency, this circuit supplies a pure emissive high-frequency current, thus exempt of harmonics, which ensures an effective transmission to the points or areas 16 of the applicator probes 10.

The circuit 21 is connected to the current lead-ins 11 of the applicator probes 10 via switches 23, under control of a bistable trigger circuit 22 which operates to provide a dephased supply to the two applicator probes 10. It is thus possible to use the two applicator probes 10 for the simultaneous treatment of two parts of the body, for instance two legs or arms.

FIG. 3 shows a flexible applicator probe 30 having three generally flat coils 12A, 12B and 12C, arranged side-by-side, and which occupy substantially the entire surface area of the flexible applicator probe 30, except for its non-conductive periphery 17.

This flexible applicator probe 30 is connected by the current lead-ins 11 of the three coils 12A, 12B and 12C to the high-frequency generator circuit 21 via three switches 23 under the control of a counter circuit 24 driven by a clock circuit 25, so as to provide a dephased supply of the three coils 12A, 12B and 12C by so-called "sectorial scanning", i.e. the high-frequency current successively sweeps or scans the three coils. The structure of the applicator probe 30, with the generally flat coils 12A, 12B and 12C molded in a sandwich configuration between a back made up of an imperforate sheet and an openwork sole, is similar to what is described in relation to FIG. 2. To simplify, only the periphery 17 is visible in FIG. 3. Of course, the use of three coils 12A, 12B and 12C permits a substantial increase in the number of discrete emission points or areas.

It is also possible to use simultaneously several flexible applicator probes 30 with multiple coils for treating different parts of the body. It it advantageous in this case to connect the applicator probes 30 by pairs to the high-frequency generator circuit 21, with one of the probes of each pair connected to the main or active output of the circuit, and the other probe of each pair connected to the secondary or ground output of the circuit instead of a base electrode connecting the treated person to ground. In this manner, the effective surface area treated by means of a given circuit is doubled, and it is no longer necessary to provide a separate ground electrode that has to be connected to the treated person, such as by being held by this person.

FIGS. 4, 5, 6 and 7 show a flexible applicator probe 40 comprising an oblong sheet of flexible rubber incorporating four generally flat coils 12A, 12B, 12C and 12D arranged one after the other along the length of the applicator probe 40, and which occupy substantially the entire surface area of the flexible applicator probe, except its non-conductive periphery 17.

This flexible applicator probe 40 is connected by a current lead-in 11 to a high-frequency generator, as shown in FIG. 3. This current lead-in 11 extends inside and along the applicator probe above the generally flat coils 12A, 12B, 12C and 12D and is successively connected (as illustrated for coil 12B in FIG. 6A) to the generally flat coils 12A, 12B, 12C, 12D, thus enabling a dephased supply of the four coils by "sectorial sweeping or scanning". Several coils 40 may be connected simultaneously, preferably in pairs, to the high-frequency generator, in order to simultaneously treat several parts of a body, or several persons.

In the embodiment of FIG. 7, it can be seen that the current lead-in 11 is connected to the applicator probe 40 by a reinforced corner of the periphery 17. It is also possible to situate the current lead-in centrally relative to the applicator probe, as in FIG. 4.

Figure 7A:
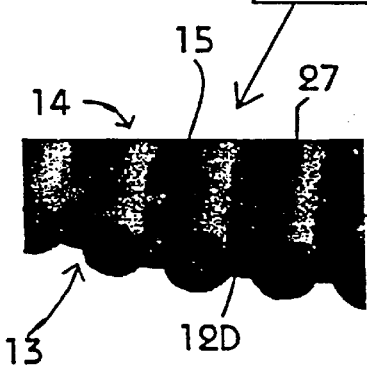
FIGS. 7A and 7B are enlargements of the framed part of FIG. 7, seen from the front and from the back.
Figure 7B:
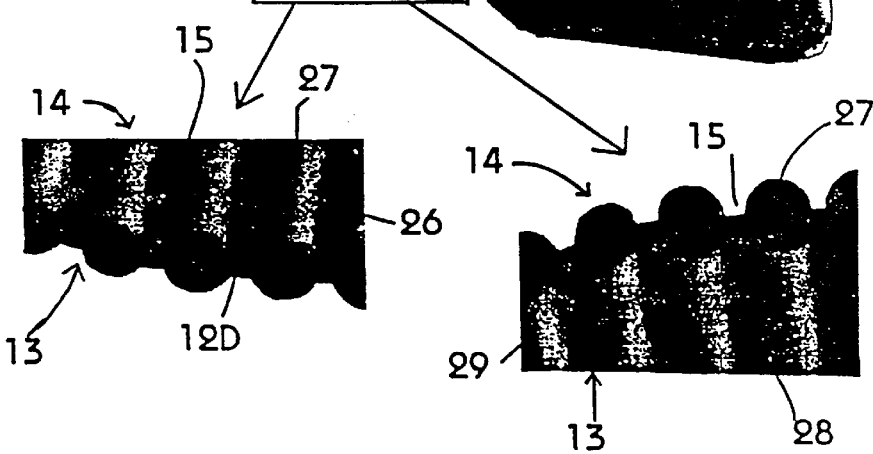

As can be seen in FIGS. 5A, 6A and 6B, the coils 12A, 12B, 12C, 12D are molded in sandwich-configuration between an openwork sole 14 and a set back (alveolar) top 13. For example, as can be seen also in FIGS. 7, 7A and 7B, the openwork cavities 15 on the side of sole 14 are formed by a criss-cross of tranverse elements 26 and longitudinal elements 27. On the top side 13, not-quite-so deep closed waffle-like cavities are formed by transverse elements 28 and longitudinal elements 29, and these do not allow access to the coils. On side 14, the longitudinal elements 27 are of the same height as the periphery 17, with the transverse elements 26 slightly inset (set back); on side 13, the longitudinal elements 29 and transverse elements 28 are of the same height, slightly inset (set back) relative to the periphery 17. Of course, other configurations are possible.

The dimensions of the openwork cavities 15 in sole 14 and the closed cavities in top 13 progressively increase in the direction along the applicator probe 40 (see the progressive spacing of the transverse elements 26/28 in FIGS. 6A and 6B). For example, in the case of an applicator probe 40 measuring about 10 cm×30 cm, comprising four coils with eighteen "arms" as illustrated in FIG. 4, there are eighteen rows of cavities and each row may include for instance from 40 to 60 cavities, or more, whose length increases from about 1 mm to 3 mm adjacent the current lead-in side (ses FIG. 6A), up to a length of about 3 mm to 5 mm at the free end of the applicator probe 40 (see FIG. 4B). The width of these cavities may be constant or may increase progressively in the width direction of applicator probe 40.

This double-sided applicator probe 40 with cavities of different dimensions on its two faces has numerous advantages. A first advantage is that it procures a greater flexibility than the single-faced applicator probes 10, 30. A second advantage resulting from the progresive increase in the dimensions of the cavities is that it enables a uniform thermal distribution, hence a uniform treatment along the applicator probe. Moreover, due to the different depths of the cavities on the opposite faces of the applicator probe, different quantities of the gel/product mixture can be applied according to the treatment mode. Finally, the open cavities 15 on the face of sole 14 enable contact to be made between the exposed points of the coils and the gel/product mixture, whereas the closed cavities on the face of top 13 are insulated from the coil's turns, allowing an attenuated transmission of the flux of electromagnetic energy for certain types of treatment for which the product does not have to penetrate down to the roots.

The arrangement of the generally flat coils of the applicator probes 10, 30, 40 of FIGS. 1, 3 and 4 is given solely by way of example. Alternatively, it is possible to provide generally flat coils whose generally flat turns extend across the short side of an oblong rectangular flexible applicator probe. The number of generally flat turns of each coil may be between three and ten, or more. It is also possible to provide flexible applicator probes of other shapes: oblong, square, circular, ovoid, etc.

The loaded gel used for the treatment method is preferably composed of a non-polymerisable conductive gel of a type used usually for coupling ultrasound probes with the skin, mixed with a bioactive product. The gel has a neutral pH and is for example based on a polymer of 5-bromo-5-nitro-1,3-dioxane-2-carboxyvinylic ester. The composition of the bioactive product depends on the desired action. For depilation, one may choose a product providing a progressive atrophy of the hair root, for example a post-depilatory lotion of the type usually used immediately after wax-depilation, as well as during the subsequent days. Such lotions comprise plant extracts, essential oils, demineralised water and possibly other components, for example polyoxyethylenes. These products, known sometimes as "hair regrowth moderators" are non-toxic and generally risk-free when used.

For treating baldness, the gel can be mixed with, for example, minoxydil, or any other product promoting hair regrowth. A mixture of 50:50 volume % of gel and minoxydil has given satisfactory results.

In order not to diminish the conductive properties of the gel, the quantity of active or treating product will in general not exceed 50 weight % of the gel, usually less than 25% (% by weight=% by volume). Alcohol, sodium chloride and/or other substances may be added to improve the conductivity of the product and/or as conserving agents.

Tests have shown that applying high-frequency energy to the bioactive product alone or to the gel alone does not produce any special effect, whereas with the mixture a good penetration of the bioactive product carried by the conductive solution derived from the gel is obtained. It appears that the flow of electromagnetic and electric energy follows the path of least resistance: through the gel and conductive lotion mixture applied to the surface of the skin, and then, around the hair root, only through the conductive lotion which alone penetrates into the pore. The gel allows a progressive release of the active lotion and penetration thereof, under the conjugated action of the electromagnetic and electric fields.

The flux of electromagnetic energy produced by the high-frequency current has an excellent coefficient of absorption in the skin, because the system behaves like a radio transmitter-receiver. For this purpose, a pure high-frequency emissive current, exempt of harmonics, is preferably used.

The energy of the high-frequency current is focalised onto the skin by the emission points or areas 16 situated on the face of the flexible applicator probes 10, 30, 40 which is in contact with the loaded gel. This energy follows the conductive solution and carries with it the active product into the follicle, causing a progressive heating accompanied by dilatation of the hair follicle, which favors the penetration of the active product and increases the effectiveness of the latter's action on the hair root. This produces intraroot ionothermolysis of the hair, by effective penetration of the conductive and bioactive solution.

Unlike the handleable, rigid probes used up to now, the flexible or morphological applicator probe according to the invention permits the application of a controlled quantity of conductive gel onto a large surface area of the skin and the use of a very large number of emitting points or areas 16.

It thus suffices to apply the gel onto the alveolar surface of the flexible applicator probe and/or onto the skin, and to install the flexible applicator probes 10, 30 and/or 40. After a treatment of several minutes, a softening of the hair follicle takes place and, in the case of a depilatory treatment, atrophy of the hair root occurs, thus assisting its extraction by the classic means of cold wax, for example, or even in certain cases, by simple washing. Several sessions are necessary to produce permanent atrophy of the hair.

The multiplicity of small cavities and small points for the electromagnetic emission, in the large surface of the flexible applicator probe enables a micro-action over a large quantity of the gel/product mixture for a sufficient duration to promote disintegration of the gel/product by liquefaction of the gel and evaporation of micro-parrticles. The efficiency of this micro-action will be all the greater as the dimension of the cavities and of the emitting points is reduced, and this results in an increased efficiency of penetration of the product.

For hair regrowth, the same method of application serves to cause penetration of the treating product into the hair root and increases its effectiveness. This method applies not only for the regrowth of the scalp's natural hair, but also to transplanted hair to increase the effectiveness of the transplant.

In an improved permanent depilation method, before applying the mixture, the hairs extending over an area of the skin to be treated are cut, leaving the severed ends of the hairs flush with the surface of the skin, for example projecting by about 1 mm. For this, a conventional hair trimmer is used; shaving is not recommended. The gel/product mixture and a flux of high-frequency electromagnetic energy are then applied, preferably using a flexible alveolar applicator probe according to this invention. This treatment causes the product to penetrate down to the roots of the cut hairs. The treatment is repeated after a rest period, for instance of several days, or even a week, possibly without cutting the hairs again. This treatment is continued until the hair roots have completely atrophied and the hairs with their roots preferably fall out naturally, for example when being washed. This method leads to a permanent depilation after fewer treatment sessions. Moreover, clients can leave a beauty parlor after their first treatment session with their skin looking nice, even though the treatment is not finished.

The applicator probes 10, 30, 40 each comprise a large number of conductive points or areas 16 of focalised emission that contact the loaded gel. It is possible to apply the gel to the skin, then install the flexible applicator probe 10,30, 40. Preferably, however, the gel is applied to the applicator probe's sole 14, then the applicator probe's sole is applied to the skin directly or covered with the mixture. During the treatment it is possible to hold the flexible applicator probe in place on the skin using a sheet of plastic material that maintains adequate humidity for the entire duration of the treatment.

The points or areas 16 accessible through the openings 15 form electrical and electromagnetic conduction windows leading into the the conductive gel, and also form cavities for receiving the gel/product mixture. These points or areas 16 are preferably aligned in one or more rows along the rectangular sole 14, thereby forming an alveolar contact surface. Though other arrangements are possible, providing several rows of points or areas 16 has the advantage that it enables the treatment of large surface areas, while avoiding possible interferences, especially when a supply by sectorial sweeping or scanning is used.

To enable effective treatments on different parts of the body, and effective treatments of different types of pilosity, several flexible applicator probes 10, 30, 40 of similar or different shapes and dimensions may be selectively and removably attached to different parts of the body, these applicator probes being preferably connected by pairs to the active output and to the neutral or ground of the high-frequency generator circuit.

It is also possible to provide handleable rigid probes according to WO 93/04636 as well as a needle fitment interchangeable with the flexible applicator probes, enabling the use of applicator probes of special shapes for delicate parts of the body as well as, in certain cases, the use of the classic high-frequency depilation method using a needle, employing the same high-frequency supply circuit.

I claim:

1. An applicator probe for applying a flux of high-frequency electromagnetic energy to the skin, the applicator probe being provided with a non-conducting contact surface adapted to be applied to the skin and having
a plurality of discrete conductive electromagnetic emissive areas formed by parts of turns of a coil, said coil being set back in relation to said non-conducting contact surface, characterized in that said non-conducting contact surface is in the form of a flexible sheet able to conform to the part of the body to which it is applied, this sheet comprising
non-conductive lower and upper parts,
said non-conducting contact surface being present at least on said lower part and
being provided with cavities, each of said cavities having a cavity floor, and in that the coil has generally flat turns arranged in sandwich configuration between said lower part and said upper part with the emissive areas arranged at the cavity floor of each of said cavities in the non-conducting contact surface.

2. A flexible applicator probe according to claim 1, wherein said generally flat turns of said coil occupy substantially the entire surface of the flexible sheet, except for a non-conducting periphery of the sheet.

3. A flexible applicator probe according to claim 1, comprising several coils whose generally flat turns occupy substantially the entire surface of the flexible sheet, except for a non-conducting periphery of the sheet.

4. An elongated flexible applicator probe according to claim 3, comprising several coils with generally flat turns arranged one after another along the length of the applicator probe.

5. A flexible applicator probe according to claim 1, wherein said cavities are of varying size over the contact surface of the applicator probe.

6. A flexible applicator probe according To claim 1, wherein said discrete conductive electromagnetic emission areas are formed by exposed parts of the turns of at least one generally flat coil which open into cavity-forming orifices in this surface.

7. A flexible applicator probe according to claim 1, further comprising an upper contact surface on said upper part.

8. A flexible applicator probe according to claim 7, wherein said upper part has cavities which differ in geometry from the cavities on the lower part.

9. A flexible applicator probe according to claim 7, wherein said upper part has cavities which differ in distribution from the cavities on the lower part.

10. A flexible applicator probe according to claim 1, wherein the cavities in the non-conducting contact surface are aligned in rows, forming an alveolar contact surface.

11. A method of cosmetic treatment of the skin, using a flexible applicator probe according to claim 1, wherein a conductive gel loaded with an active ingredient is applied to a surface selected from a group consisting of the skin to be treated and the non-conducting contact surface, and said non-conductive contact surface is applied to the skin to be treated to cause the cosmetic bio-active treatment product to penetrate into the pores of the skin down to the hair roots by the high-frequency flux of energy emitted by said emissive areas.

12. The method of claim 11 wherein said active ingredient is a hair-regenerating product.

13. A method according to claim 11, characterized in that said loaded gel is applied into cavities provided in the surface of the flexible applicator probe.

14. The method of claim 11 wherein said active ingredient is a cosmetic bio-active treatment product.

15. The method of claim 11 wherein said active ingredient is a product able to atrophy the hair roots.

16. A depilation method according to claim 15, characterized in that before applying the loaded conductive gel to the skin, the hairs over an area of the skin to be treated are cut, leaving the severed ends of the hairs flush with the surface of the skin, the loaded gel and the flux of high-frequency electromagnetic energy are then applied to cause the product to penetrate down to the roots of the cut hairs, and the treatment is repeated after a rest period, possibly without cutting the hairs again, until the hair roots have completely atrophied and the hairs with their roots preferably fall out naturally.

* * * * *